United States Patent
Rouleau et al.

(12)

(10) Patent No.: US 6,337,063 B1
(45) Date of Patent: Jan. 8, 2002

(54) PROCESS FOR PREPARING A ZEOLITE WITH STRUCTURE TYPE EUO USING STRUCTURING AGENT PRECURSORS AND ITS USE AS AN AC8 ISOMERISATION CATALYST

(75) Inventors: Loïc Rouleau, Oullins; Sylvie Lacombe, Rueil-Malmaison; Fabio Alario, Neuilly sur Seine; Elisabeth Merlen, Rueil-Malmaison; Frédéric Kolenda, Francheville le Haut; Julia Magne-Drisch, Vilette de Vienne, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/432,122

(22) Filed: Nov. 2, 1999

(30) Foreign Application Priority Data

Nov. 2, 1998 (FR) .............................. 98-13773
Dec. 23, 1998 (FR) .............................. 98-16411

(51) Int. Cl.$^7$ ......................... C01B 39/04; B01D 53/02
(52) U.S. Cl. ...................... 423/705; 423/708; 423/709; 95/90
(58) Field of Search ................................ 423/705, 708, 423/709; 502/66, 74, 73; 95/90

(56) References Cited

U.S. PATENT DOCUMENTS

| 4,537,754 A | * | 8/1985 | Casci et al. |
| 4,640,829 A | * | 2/1987 | Rubin |
| 4,695,667 A | * | 9/1987 | Sumitani et al. |
| 4,721,609 A | * | 1/1988 | Baake et al. |
| 4,741,891 A | * | 5/1988 | Casci et al. |
| 6,057,486 A |   | 5/2000 | Merlen et al. |

FOREIGN PATENT DOCUMENTS

| EP | 0 042 226 | 12/1981 |
| EP | 0 051 318 | 5/1982 |
| EP | 0 463 768 | 1/1992 |
| WO | WO 96/29284 | 9/1996 |

* cited by examiner

Primary Examiner—David R. Sample
(74) Attorney, Agent, or Firm—Millen, White, Zelano & Branigan, P.C.

(57) ABSTRACT

A process for synthesising a zeolite with structure type EUO comprising at least one element X selected from silicon and germanium and at least one element T selected from aluminum, iron, gallium, boron, titanium, vanadium, zirconium, molybdenum, arsenic, antimony, chromium and manganese, comprises reacting an aqueous mixture comprising at least one source of at least one element X, at least one source of at least one element T, and at least one precursor of an organic compound comprising at least one alkylated polymethylene α-ω diammonium derivative, wherein at least one precursor is selected from monoamines. The zeolite obtained is used as a catalyst in a process for converting hydrocarbon-containing feeds, as an adsorbent to control pollution and as a molecular sieve for separation, and particularly for isomerising aromatic compounds containing 8 carbon atoms.

18 Claims, No Drawings

PROCESS FOR PREPARING A ZEOLITE WITH STRUCTURE TYPE EUO USING STRUCTURING AGENT PRECURSORS AND ITS USE AS AN AC8 ISOMERISATION CATALYST

CROSS-REFERENCE TO RELATED APPLICATION

This application is related to applicants concurrently filed application Ser. No. 09/432,120, entitled "Process For Preparing A Zeolite With Structure Type EUO Using Zeolitic Material Seeds And Its Use As An AC8 Isomerisation Catalyst", based on French Applications 98/13.839 filed Nov. 2, 1998 and 98/16.412 filed Dec. 23, 1998.

TECHNICAL FIELD

The present invention relates to a novel process for preparing zeolites with structure type EUO. Zeolites with structure type EUO synthesised using the process of the present invention include EU-1 and TPZ-3 zeolites. These zeolites generally have the following formula in the anhydrous form: 0 to 20 $R_2O$: 0–10 $T_2O_3$: 100$XO_2$ where R represents a monovalent cation or 1/n of a valency cation n, T represents at least one element selected from aluminum, iron, gallium, boron, titanium, vanadium, zirconium, molybdenum, arsenic, antimony, chromium and manganese, and X represents silicon and/or germanium.

Zeolites with structure type EUO such as EU-1 and TPZ-3 zeolites are generally synthesised by mixing, in an aqueous medium, at least one source of silica and/or germanium and at least one source of at least one element selected from aluminium, iron, gallium, boron, titanium, vanadium, zirconium, molybdenum, arsenic, antimony, chromium and manganese in the presence of an organic compound comprising an alkylated polymethylene $\alpha a$-$\omega$ diammonium derivative, acting as a structuring agent. The mixture is generally maintained at a certain temperature until the zeolite crystallises.

The present invention also relates to a catalyst based on a zeolite with structure type EUO, said zeolite being obtained using the novel synthesis mode described above, and to a process for preparing said catalyst. The invention also relates to a process for isomerising aromatic compounds containing 8 carbon atoms also known as "aromatic C8 cuts" in the presence of this catalyst based on a zeolite with structure type EUO.

Isomerising ethylbenzene to xylenes requires the presence of a group VIII metal. Optimised formulations based on mordenite and a group VIII metal result in catalysts for which side reactions remain non negligible. Examples which can be cited are naphthene ring opening reactions followed or otherwise by cracking or dismutation and transalkylation of C8 aromatic compounds, which lead to the formation of undesirable aromatic compounds. The discovery of new, more selective catalysts is thus of particular importance.

PRIOR ART

The EU-1 zeolite with structure type EUO, which has already been described in the prior art, has a unidimensional microporous framework, with a pore diameter of 4.1×5.7 Å (1 Å=1 Angström=$10^{-10}$ m) ("Atlas of Zeolite Structure Types", W. M. Meier and D. H. Olson, 4$^{th}$ edition, 1996). Further, N. A. Briscoe et al. stated in their article in the review Zeolites (1988, 8, 74) that such unidimensional channels have lateral pockets with a depth of 8.1 Å and a diameter of 6.8×5.8 Å. A method for synthesising EU-1 zeolite and its physico-chemical characteristics have been described in European patent EP-A-0 042 226. The synthesis mode comprises mixing a silicon and/or germanium oxide and an oxide of at least one element selected from aluminium, iron, gallium and boron in the presence of a structuring agent comprising at least one alkylated polymethylene $\alpha$-$\omega$ diammonium derivative with formula $R_1R_2R_3N^+(CH_2)_nN^+R_4R_5R_6$, the degradation products of said derivative or precursors of said derivative. The precursors of the alkylated derivative are the related diamine conjointly with alcohols or alkyl halides.

EP-A-0 051 318 relates to TPZ-3 zeolite which, according to the "Atlas of Zeolite Structure Types", W. M. Meier and D. H. Olson, 4$^{th}$ edition, 1996, has the same EUO structure type as EU-1 zeolite. Preparation of the zeolite comprises mixing a soluble alkali metal compound, a 1,6-N,N,N',N',N'-hexamethythexamethylenediammonium compound, a compound which can provide silicon and a compound which can provide alumina, at a temperature of more than 80° C.

SUMMARY OF THE INVENTION

The present invention concerns a novel process for preparing a zeolitic material with structure type EUO in the presence of at least one precursor of an alkylated polymethylene $\alpha$-$\omega$ diammonium derivative acting as a structuring agent selected from monoamines. The present invention also concerns the use of said zeolite in a catalyst also comprising at least one element from group VIII of the periodic table and at least one binder. Said catalyst can be used in a process for isomerising aromatic compounds containing 8 carbon atoms.

IMPORTANCE OF THE INVENTION

The process of the invention can reduce the zeolite crystallisation time after forming the mixture, which reduces the costs. Further, the use of precursors of the structuring agent of the invention improves safety when synthesising the zeolite, said precursors being less dangerous than the structuring agent itself or than prior art precursors, and can also reduce the cost of the reactants, said precursors being cheaper than the structuring agent itself and than prior art precursors.

Thus, surprisingly, the Applicant has discovered that synthesis of a zeolite characterized by using specific precursors of the structuring agent can produce the advantages cited above, i.e., an advantage as regards time, safety and reactant costs.

DESCRIPTION OF THE INVENTION

The invention concerns a process for synthesising a zeolite material with structure type EUO comprising mixing, in an aqueous medium, at least one source of at least one element selected from silicon and germanium and at least one source of at least one element T selected from aluminium, iron, gallium, boron, titanium, vanadium, zirconium, molybdenum, arsenic, antimony, chromium and manganese, in the presence of at least one precursor of an alkylated polymethylene $\alpha$-$\omega$ diammonium derivative acting as a structuring agent. The mixture is generally maintained at a certain temperature until the zeolite crystallises. The invention is characterized in that at least one precursor of the alkylated polymethylene $\alpha$-$\omega$ diammonium derivative selected from monoamines is used.

The alkylated polymethylene α-ω diammonium derivative acting as a structuring agent has the following formula:

$$R_1R_2R_3N^+(CH_2)_nN^+R_4R_5R_6$$

where n is in the range 3 to 14 and $R_1$ to $R_6$, which may be identical or different, can represent alkyl or hydroxyalkyl radicals containing 1 to 8 carbon atoms; up to five $R_1$ to $R_6$ radicals can be hydrogen.

In addition to the precursor(s) of the structuring agent selected from monoamines in the process of the present invention, other structuring agent group(s) are generally introduced using any suitable precursor to obtain a quaternary amnmonium compound. These precursors are of F-R-F' type where F and F' are identical or different starting groups such as an alcohol function or a halide. As an example, an additional precursor can be selected which is at least one compound selected from alkanediols and alkane dihalides.

The precursors of the structuring agent of the invention and the other precursors can be pre-heated together in the reaction vessel or they can be mixed as they are with the other reactants. The precursors can be introduced at any moment of the zeolite preparation.

Preferably, the structuring agent precursors are introduced in solution before adding the other reactants necessary to synthesise the zeolite.

In one particular implementation, it may be advantageous to add seeds S of at least one zeolite to the reaction medium. Seeds with the EUO zeolite structure type or the structure type of other accessible and cheap zeolites such as zeolites with structure type LTA, FAU, MOR or MFI can be added. These seeds can accelerate crystallisation of the EUO zeolite from the reaction mixture. The seeds can be introduced at any point of the zeolite synthesis. Preferably, in the optional case where the EUO zeolite is synthesised using seeds, said seeds are added after at least partial homogenisation of the mixture containing the other reactants.

In a further particular implementation, independent or otherwise of the preceding implementation, it may be advantageous to add at least one alkali metal or ammonium salt P to the reaction medium. Examples which can be cited are strong acid radicals such as bromide, chloride, iodide, sulphate, phosphate or nitrate, or weak acid radicals such as organic acid radicals, for example citrate or acetate. This salt can accelerate crystallisation of EUO zeolites from the reaction mixture.

The aqueous reaction mixture generally has the following molar composition, expressed in the oxide form:

| | |
|---|---|
| $XO_2/T_2O_3$ (mol/mol) | at least 10 |
| $OH^-/XO_2$ (mol/mol) | 0.002 to 2.0 |
| $Q/XO_2$ (mol/mol) | 0.002 to 2.0 |
| $Q/(M^+ + Q)$ (mol/mol) | 0.1 to 1.0 |
| $H_2O/XO_2$ (mol/mol) | 1 to 500 |
| $P/XO_2$ (mol/mol) | 0 to 5 |
| $S/XO_2$ (g/g) | 0 to 0.1 |

Preferably, the reaction mixture has the following composition, expressed in the oxide form:

| | |
|---|---|
| $XO_2/T_2O_3$ (mol/mol) | at least 12 |
| $OH^-/XO_2$ (mol/mol) | 0.005 to 1.5 |
| $Q/XO_2$ (mol/mol) | 0.005 to 1.5 |
| $Q/(M^+ + Q)$ (mol/mol) | 0.1 to 1.0 |
| $H_2O/XO_2$ (mol/mol) | 3 to 250 |
| $P/XO_2$ (mol/mol) | 0 to 1 |
| $S/XO_2$ (g/g) | 0.0005 to 0.07 | and still more preferably, the reaction mixture has the following composition, expressed in the oxide form:

| | |
|---|---|
| $XO_2/T_2O_3$ (mol/mol) | at least 15 |
| $OH^-/XO_2$ (mol/mol) | 0.01 to 1 |
| $Q/XO_2$ (mol/mol) | 0.01 to 1 |
| $Q/(M^+ + Q)$ (mol/mol) | 0.1 to 1.0 |
| $H_2O/XO_2$ (mol/mol) | 5 to 100 |
| $P/XO_2$ (mol/mol) | 0 to 0.25 |
| $S/XO_2$ (g/g) | 0.001 to 0.04 | where X is silicon and/or germanium,

T is at least one element selected from aluminium, iron, gallium, boron, titanium, vanadium, zirconium, molybdenum, arsenic, antimony, chromium and manganese;

$M^+$ represents an alkali metal or an ammonium ion;

Q represents the alkylated polymethylene α-ω diammonium derivative cited above, introduced by means of the corresponding appropriate precursors, containing a monoamine;

S represents zeolite seeds expressed in their dried, calcined or exchanged form;

P represents the alkali metal or ammonium salt.

M and/or Q can be present in the form of hydroxides or salts of inorganic or organic acids provided that the $OH/XO_2$ criterion is satisfied.

The invention is characterized in that the organic structuring agent comprising an alkylated polymethylene α-ω diammonium derivative is introduced using at least one precursor selected from monoamines. The term "monoamine" means any organic compound with an amine function. Preferably, the precursors of the invention are selected from alkylamines containing 1 to 18 carbon atoms per molecule, preferably containing 1 to 8 carbon atoms per molecule. The alkylamines can be primary, secondary or tertiary. More particularly, the precursors are selected from trialkylamines.

The preferred starting precursors are, inter alia, those which lead to the preferred alkylated polymethylene α-ω diammonium derivatives, preferably to alkylated hexamethylenediammonium derivatives and especially to methylated hexamethylenediammonium derivatives, more preferably still 1,6-N,N,N,N',N',N',-hexamethylhexamethylenediammonium salts with formula $(CH_3)_3N^+(CH_2)_6N^+(CH_3)_3$, for example the halide, hydroxide, sulphate, silicate or aluminate. As an example, and preferably, the precursor of the invention selected from monoamines is trimethylamine and the other precursor is dibromohexane.

The preferred alkali metal ($M^+$) is sodium. The preferred element T is aluminium. The preferred element X is silicon.

The silicon source can be any one in normal use envisaged for zeolite synthesis, for example solid powdered silica, silicic acid, colloidal silica or dissolved silica. Powdered silicas which can be used include precipitated silicas, in particular those obtained by precipitation from a solution of an alkali metal silicate such as Zeosil or Tixosil produced by Rhône-Poulenc, fumed silicas such as aerosil produced by Degussa and Cabosil produced by Cabot, and silica gels. Colloidal silicas with a variety of granulometries can be used, such as those sold under trade marks "LUDOX" from Dupont, and "SYTON" from Monsanto. Particular dissolved silicas which can be used are commercially available soluble glasses or silicates containing: 0.5 to 6.0 and in particular 2.0 to 4.0 moles of $SiO_2$ per mole of alkali metal oxide and silicates obtained by dissolving silica in an alkali metal hydroxide, a quaternary ammonium hydroxide or a mixture thereof More advantageously, the aluminium source is sodium aluminate, but it can be aluminium, an aluminium salt, for example a chloride, nitrate or sulphate, an aluminium alcoholate or alumina itself which should preferably be in a hydrated or hydratable form, such as colloidal alumina, pseudoboehmite, boehmite, gamma alumina or a trihydrate.

Mixtures of the sources cited above can be used. Combined sources of silicon and aluminium can also be used, such as amorphous silica-aluminas or certain clays.

The reaction mixture is normally caused to react under autogenous pressure, optionally adding a gas, for example nitrogen, at a temperature in the range 85° C. to 250° C. until zeolite crystals form, which can take from 1 minute to several months depending on the reactant composition, the mode of heating and the mixture, the working temperature and the degree of stirring. Stirring is optional but preferable, as it reduces the reaction time.

When the reaction is over, the solid phase is collected on a filter and washed and is then ready for subsequent operations such as drying, calcining and ion exchange.

To obtain the hydrogen form of the EUO zeolite, ion exchange can be carried out using an acid, in particular a strong mineral acid such as hydrochloric, sulphuric or nitric acid, or with an ammonium compound such as ammonium chloride, sulphate or nitrate. Ion exchange can be carried out by diluting once or more with the ion exchange solution. The EUO zeolite can be calcined before or after ion exchange or between two ion exchange steps, preferably before ion exchange to eliminate all absorbed organic substances, provided that ion exchange is thereby facilitated.

As a general rule, the cation or cations of the EUO zeolite can be replaced by one or more cations of any metal, in particular those from groups IA, IB, IIA, IIB, IIIA and IIIB (including the rare earths), VIII (including the noble metals), also lead, tin and bismuth (the periodic table is that shown in the "Handbook of Physics and Chemistry", $76^{th}$ edition). Exchange is carried out using any water-soluble salt containing the appropriate cation.

The present invention also concerns the use of the EUO zeolite prepared using the process of the present invention as an adsorbent to control pollution, as a molecular sieve for separation and as an acidic solid for catalysis in the fields of refining and petrochemistry.

As an example, when it is used as a catalyst, the EUO zeolite synthesised using the process of the present invention can be associated with an inorganic matrix which can be inert or catalytically active, and with an active phase. The inorganic matrix can be present simply as a binder to keep the small particles of zeolite together in the different known forms of catalysts (extrudates, beads, powders), or can be added as a diluent to impose a degree of conversion on a process which would otherwise proceed at too high a rate leading to clogging of the catalyst as a result of increased coke formation. Typical inorganic diluents are support materials for catalysts such as silica, the different forms of alumina and kaolinic clays, bentonites, montmorillonites, sepiolite, attapulgite, fuller's earth, synthetic porous materials such as $SiO_2$—$Al_2O_3$, $SiO_2$—$ZrO_2$, $SiO_2$—$ThO_2$, $SiO_2$—$BeO$, $SiO_2$ or any combination of these compounds.

The zeolite with structure type EUO can also be associated with at least one other zeolite and acts as the principal active phase or as an additive.

The inorganic matrix can be a mixture of different compounds, in particular an inert phase and an inorganic phase.

The metallic phase is introduced into the zeolite alone, the inorganic matrix alone or into the inorganic matrix-zeolite ensemble, by ion exchange or impregnation with cations or oxides selected from the following: Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Ru, Rh, Os, Ir and any other element from the periodic table.

Catalytic compositions comprising the zeolite with structure type EUO can be applied to isomerisation, transalkylation and dismutation, alkylation and dealkylation, hydration and dehydration, oligomerisation and polymerisation, cyclisation, aromatisation, cracking and hydrocracking, hydrogenation and dehydrogenation, reforming, oxidation, halogenation, amine synthesis, hydrodesulphurisation and hydrodenitrogenation, catalytic elimination of oxides of nitrogen, ether formation and hydrocarbon conversion and to the synthesis of organic compounds in general, these reactions involving saturated and unsaturated aliphatic hydrocarbons, aromatic hydrocarbons, oxygen-containing organic compounds and organic compounds containing nitrogen and/or sulphur, also organic compounds containing other functional groups.

More particularly, the present invention concerns a catalyst for isomerising aromatic C8 compounds. The catalyst of the present invention, formed into beads or extrudates, contains:

at least one zeolite with an EUO structure, for example EU-1 zeolite, characterized in that during synthesis, at least one precursor of the alkylated polymethylene α-ω diammonium derivative is used, selected from monoamines using the method described above;

at least one metal from group VIII of the periodic table, preferably selected from the group constituted by palladium and platinum and still more preferably platinum;

at least one binder, preferably alumina;

optionally, at least one metal from the group formed by elements from groups IB, IIB, IIIA, IVA, VIB and VIIIB of the periodic table, preferably tin or indium;

optionally, sulphur; said catalyst being characterized in that it is prepared using a novel mode for synthesising the zeolite with structure type EUO as described above.

More precisely, the catalyst prepared using the process of the present invention, formed into beads or extrudates, comprises, with respect to the catalyst weight:

1% to 90%, preferably 3% to 60% and more preferably 4% to 40% by weight of at least one zeolite with structure type EUO, obtained using the novel synthesis mode, comprising at least one element X selected from germanium and silicon and at least one element T selected from the group formed by aluminium, iron, gallium, boron, titanium, vanadium, zirconium, molybdenum, arsenic, antimony, chromium and manganese, preferably aluminium and boron, with an atomic ratio X/T being 5 or more. Said zeolite is at least partially in the acidic form, i.e., in the hydrogen ($H^+$) form, the sodium content being such that the Na/T atomic ratio was less than 0.5, preferably less than 0.1, more preferably less than 0.02;

0.01% to 2% and preferably 0.05% to 1.0% by weight of at least one metal from group VIII of the periodic table, preferably selected from the group formed by platinum and palladium and more preferably platinum;

optionally, 0.01% to 2%, preferably 0.05% to 1.0% by weight of at least one metal from the group formed by groups EB, IIB, IIIA, IVA, VIB and VIIB of the periodic table, preferably selected from the group formed by tin and indium;

optionally, sulphur the quantity of which is such that the ratio of the number of sulphur atoms to the number of deposited group VIII metal atoms is in the range 0.5 to 2, limits included;

the complement to 100% by weight of at least one binder, preferably alumina.

Any zeolite with structure type EUO which is known to the skilled person and obtained using the synthesis mode described in the present patent is suitable for the catalyst prepared using the process of the present invention. Thus, for example, the zeolite used as a base to prepare said catalyst can be as synthesised EU-1 zeolite having the required specificities regarding the X/T ratio. Generally, calcining can then be carried out, then at least one ion exchange in at least one $NH_4NO_3$ solution so as to obtain a zeolite with a greater or lesser residual sodium content.

The binder (or matrix) in the catalyst prepared using the process of the present invention generally consists of at least one element selected from the group formed by clays, magnesia, aluminas, silicas, titanium oxide, boron oxide, zirconia, aluminium phosphates, titanium phosphates, zirconium phosphates and silica aluminas. Charcoal can also be used. Preferably, the binder is alumina.

The zeolite with structure type EUO, for example EU-1 zeolite, in the catalyst of the invention, is at least partially, preferably practically completely in its acid form, i.e., in the hydrogen form ($H^+$), the sodium content preferably being such that the Na/T atomic ratio is less than 0.5, preferably less than 0.1, more preferably less than 0.02.

The metals can be introduced either all in the same way or using different techniques, at any time in the preparation, before or after forming and in any order. Further, intermediate treatments such as calcining and/or reduction can be carried out between depositions of the different metals.

At least one group VIII element is introduced into the zeolite or onto the binder, preferably onto the binder before or after forming.

One preferred method consists of producing a mixture of the matrix and the zeolite followed by forming. Forming is generally followed by calcining, generally at a temperature in the range 250° C. to 600° C., limits included. At least one element from group VIII of the periodic table is introduced after this calcining, preferably by selective deposition onto the binder. Said elements are in practice deposited in an amount of more than 90% in total on the binder and in a manner which is known to the skilled person by controlling the parameters used during said deposition, such as the nature of the precursor used to carry out said deposition. Optionally, at least one element from the group formed by elements from groups IB, IIB, IIIA, IVA, VIB and VIIB are added. Elements from group VIII and groups IB, IIB, IIIA, IVA, VIB and VIIB are added either separately at any stage of the catalyst preparation, or simultaneously in at least one unitary step. When an element from at least one of groups IB, IIB, IIIA, IVA, VIB and VIIB is separately added, then preferably it is added prior to adding the group VIII element.

At least one group VIII element is deposited, preferably onto the zeolite-binder mixture which has already been formed by any process known to the skilled person. Such deposition is, for example, carried out using a dry impregnation step, excess impregnation or ion exchange. Any precursor can be used to deposit these elements. As an example, and preferably, anionic exchange is carried out with hexachloroplatinic acid and/or hexachloropalladic acid in the presence of a competing agent, for example hydrochloric acid. With such precursors, the metal is in practice deposited in an amount of more than 90% in total onto the binder and it has a good dispersion and good macroscopic distribution through the catalyst grain which constitutes the preferred preparation method.

Optionally, at least one other metal selected from the group formed by elements from groups IB, IIB, IIIA, IVA, VIB and VIIB of the periodic table is also introduced. Any of the deposition techniques known to the skilled person and any precursor can be used to introduce at least one additional metal.

One preferred method for preparing the catalyst, prepared using the process of the invention, consists of milling the zeolite in a moist gel of matrix (generally obtained by mixing at least one acid and powdered matrix), for example alumina, for a period required to obtain good homogeneity of the paste produced, namely, for example, for about ten minutes, then passing the paste through a die to form extrudates, for example with a diameter in the range 0.4 to 4 mm, limits included. Then after oven drying, for example for several hours at about 120° C., and after calcining, for example for two hours at about 500° C., at least one element, for example platinum, is deposited, for example by anion exchange with hexachloroplatinic acid in the presence of a competing agent (for example hydrochloric acid), said deposition being followed by calcining, for example for about 2 hours at about 500° C.

Platinum is generally introduced into the matrix in the form of hexachloroplatinic acid, but ammoniacal compounds or compounds such as ammonium chloroplatinate, dicarbonyl platinum dichloride, hexahydroxyplatinic acid, palladium chloride, palladium nitrate can be used for all noble metals.

In the present invention, at least one noble metal from the platinum family can, for example, be used by dint of ammoniacal compounds. In this case, the noble metal will be deposited onto the zeolite.

For platinum, examples which can be cited are platinum II tetramine salts with formula $Pt(NH_3)_4X_2$, platinum IV hexamine salts with formula $Pt(NH_3)_6X_4$; platinum IV halogenopentarnine salts with formula $(PtX(NH_3)_5)X_3$; platinum N tetrahalogenodiamine salts with formula $PtX_4(NH_3)_2$; and complexes of platinum with halogen-polyketones and halogenated compounds with formula $H(Pt(acac)_2X)$; X being a halogen selected from the group formed by chlorine, fluorine, bromine and iodine, X preferably being chlorine, and acac representing the group $C_5H_7O_2$ derived from acetylacetone.

The noble metal from the platinum family is preferably introduced by impregnation using an aqueous or organic solution of one of the organometallic compounds cited above. Of the organic solvents which can be used, paraffinic, naphthenic or aromatic hydrocarbons can be cited, and halogenated organic compounds containing, for example, 1 to 12 carbon atoms per molecule. Examples which can be cited are n-heptane, methylcyclohexane, toluene and chloroform. Mixtures of solvents can also be used.

The additional metal, optionally introduced in addition, selected from the group formed by elements from groups IB, IIB, IIIA, IVA, VIB and VIIB, can be introduced via compounds such as chlorides, bromides and nitrates, alkyls of elements from groups IB, IIB, IIIA, IVA, VIB and VIIB, namely, for example, tin and indium, alkyl tin, indium nitrate and chloride.

This metal can also be introduced in the form of at least one organic compound selected from the group formed by complexes of said metal, in particular polyketone complexes of metal and hydrocarbylmetals such as metal alkyls, cycloalkyls, aryls, alkylaryls and arylalkyls. In the latter case, the metal is advantageously introduced using a solution of an organometallic compound of said metal in an organic solvent. Metal organohalogenated compounds can also be used. Particular metal compounds which can be cited are tetrabutyltin in the case of tin, triphenylindium in the case of indium.

The impregnating solvent is selected from the group formed by paraffinic, naphthenic and aromatic compounds containing 6 to 12 carbon atoms per molecule and halogenated organic compounds containing 1 to 12 carbon atoms per molecule. Examples are n-heptane, methylcyclohexane and chloroform. It is also possible to use mixtures of the solvents defined above.

It is also possible to introduce at least one metal selected from the group formed by elements from groups IB, IIB, IIIA, IVA, VIB and VIIB. This additional metal can optionally be introduced at any time during preparation, preferably prior to deposition of one of more of the group VIII metals. If this metal is introduced before the noble metal, the metal compound used is generally selected from the group formed by the metal halide, nitrate, acetate, tartrate, carbonate and oxalate. Introduction is then advantageously carried out in aqueous solution. However, it can also be introduced using a solution of an organometallic compound, for example tetrabutyltin. In this case, before introducing at least one noble metal, calcining in air is carried out.

The catalyst of the invention is generally formed so that the catalyst is preferably put into the form of extrudates or beads to suit its application.

Preparation of the catalyst is generally finished by calcining, normally at a temperature in the range from about 250° C. to 600° C., limits included, for a period of about 0.5 to 10 hours, preferably preceded by drying, for example oven drying, at a temperature in the range from ambient temperature to 250° C., preferably in the range 40° C. to 200° C. Said drying step is preferably carried out during the rise in temperature required to carry out said calcining step.

When the catalyst of the present invention contains sulphur, sulphur is introduced into the formed, calcined catalyst containing the metal or metals cited above, either in situ before the catalytic reaction, or ex-situ. Sulphurisation can optionally be carried out after reduction. With in situ sulphurisation, if the catalyst has not already been reduced, reduction is carried out before sulphurisation. With ex-situ sulphurisation, reduction is carried out followed by sulphurisation. Sulphurisation is carried out in the presence of hydrogen using any sulphurising agent which is known to the skilled person, such as dimethyl sulphide or hydrogen sulphide. As an example, the catalyst is treated with a feed containing dimethyl sulphide in the presence of hydrogen, with a concentration such that the sulphur/metal atomic ratio is 1.5. The catalyst is then kept at about 400° C. for about 3 hours in a stream of hydrogen before injecting the feed.

The present invention also concerns a process for isomerising aromatic C8 cuts constituted by a mixture of xylenes and possibly ethylbenzene, in the presence of a catalyst comprising a zeolite prepared using the process of the present invention.

The catalyst prepared using the process of the present invention is used for isomerising an aromatic C8 cut comprising, for example, either solely a mixture of xylene (s), or solely ethylbenzene, or a mixture of xylene(s) and ethylbenzene. The process is generally carried out under the following operating conditions:

- a temperature in the range 300° C. to 500° C., limits included, preferably in the range 320° C. to 450° C. limits included, and more preferably in the range 340° C. to 430° C., limits included;
- a partial hydrogen pressure in the range 0.3 to 1.5 MPa, limits included, preferably in the range 0.4 to 1.2 MPa, limits included and more preferably 0.7 to 1.2 NPa, limits included;
- a total pressure in the range 0.45 to 1.9 MPa limits included, preferably in the range 0.6 to 1.5 MPa limits included;
- a space velocity, expressed as kilograms of feed introduced per kilogram of catalyst per hour, in the range 0.25 to 30 $h^{-1}$ limits included, preferably in the range 1 to 10 $h^{-1}$ limits included, and more preferably in the range 2 to 6 $h^{-1}$ limits included.

The catalyst used in the present invention, in the form of mechanically strong extrudates or beads, constituted by at least one zeolite with structure type EUO, for example an EU-1 zeolite, obtained by the synthesis mode described in the present invention, at least one binder, at least one metal selected from elements from group VIII of the periodic table, said metal preferably being deposited on the binder, has excellent catalytic performances in terms of activity, selectivity and stability over time for transforming hydrocarbons, such as the isomerisation of aromatic C8 cuts, i.e., mixtures constituted by xylenes and possibly ethylbenzene. The EUO type zeolites used to obtain this catalyst are obtained in much shorter synthesis times than for the EUO type zeolites described in the prior art. This particular synthesis mode thus leads to a cost advantage for manufacture of the catalyst, all the more so as the precursors used are cheaper than the structuring agent itself, and without degradation of the catalytic properties of the catalyst. Further, the precursors are less dangerous than the structuring agent thus improving safety during synthesis.

The invention will now be illustrated by the following examples.

EXAMPLES 1 TO 7 (comparative)

Synthesis of EU-1 zeolite (or TPZ-3) with a Si/Al ratio of 15 to 100 with hexamethonium (1,6-hexamethylhexamethylenediammonium) bromide as the organic structuring agent The synthesis mixture has the following molar composition:

| Example | 1<br>Si/Al =<br>15 | 2<br>Si/Al =<br>15 | 3 & 4<br>Si/Al =<br>30 | 5<br>Si/Al =<br>40 | 6<br>Si/Al =<br>70 | 7<br>Si/Al =<br>100 |
| --- | --- | --- | --- | --- | --- | --- |
| $SiO_2$ (mol) | 60 | 60 | 60 | 60 | 60 | 60 |
| $Al_2O_3$ (mol) | 2 | 2 | 1 | 0.75 | 0.43 | 0.3 |
| $Na_2O$ (mol) | 10 | 10 | 10 | 10 | 5 | 5 |
| $HxBr_2$ (mol) | 20 | 20 | 20 | 20 | 20 | 20 |
| $H_2O$ (mol) | 2800 | 2800 | 2800 | 2800 | 2800 | 2800 |
| EU-1/$SiO_2$ (g/g) | 0 | 0.04 | 0.04 | 0.04 | 0.04 | 0.04 |

$HxBr_2$ = hexamethonium bromide = $Me_3N(CH_2)_6N\ Me_3^{2+}(Br^-)_2$

A solution A composed of silica and structuring agent was prepared by diluting the hexamethonium bromide (Fluka, 97%) in 80% of the water necessary to form the gel then adding the colloidal silica sol (Ludox HS40, Dupont, 40% $SiO_2$). Solid sodium hydroxide (Prolabo, 99%) and solid sodium aluminate (Prolabo, 46% $Al_2O_3$, 33% $Na_2O$) were then dissolved in 10% of the water necessary to form the gel to form a solution B. Solution B was added to solution A with stirring, then the remaining water (10%). Mixing was carried out until the medium was homogeneous and seeds of dried EU-1 zeolite were added. The resulting mixture was reacted in a 125 ml autoclave with stirring at 180° C. under autogenous pressure. After cooling, the product was filtered and washed with 0.5 litres of demineralised water then dried in a ventilated oven at 120° C. The quantities of reactants introduced are shown in the following table:

| Example | 1 Si/Al = 15 | 2 Si/Al = 15 | 3 & 4 Si/Al = 30 | 5 Si/Al = 40 | 6 Si/Al = 70 | 7 Si/Al = 100 |
|---|---|---|---|---|---|---|
| Colloidal silica (g) | 14.50 | 14.50 | 14.52 | 14.53 | 14.61 | 14.61 |
| Sodium aluminate (g) | 0.715 | 0.715 | 0.358 | 0.269 | 0.155 | 10108 |
| Sodium hydroxide (g) | 0.985 | 0.985 | 1.139 | 1.177 | 0.584 | 0.604 |
| HxBr$_2$ (g) | 12.03 | 12.03 | 12.05 | 12.05 | 12.12 | 12.12 |
| Water (g) | 71.77 | 71.77 | 71.93 | 71.97 | 72.53 | 72.55 |
| EU-1 seeds (g) | 0 | 0.232 | 0.232 | 0.232 | 0.234 | 0.234 |

HxBr$_2$ = hexamethonium bromide = Me$_3$N(CH$_2$)$_6$N Me$_3^{2+}$(Br$^-$)$_2$

The results of X ray diffraction and chemical analysis are shown in Table 1. The syntheses of Examples 2, 3, 5, 6 and 7 carried out at 180° C. with the prior art structuring agent with EU-1 seeds led to pure EU-1 zeolite (100%±3 crystallinity) with a Si/Al ratio which was between 15 and 100, in a maximum yield (about 5%). Example 1 corresponds to a preparation without seed and required a longer crystallisation period compared with Example 2 to produce the EU-1 zeolite (125 hours as opposed to 96 hours). Example 4 produced mostly EU-1 with a little cristobalite because of too long a crystallisation period compared with Example 3 (96 hours as opposed to 72 hours).

EXAMPLES 8 TO 13 (comparative)

Synthesis of EU-1 zeolite (or TPZ-3) with a Si/Al ratio of 15 to 100 with hexamethonium iodide (1,6-hexamethylhexamethylenediammonium iodide) precursors as the organic structuring agent containing a diamine (1-6-tetramethylhexamethylene diamine and methyl iodide)

| Example | 8 Si/Al = 15 | 9 Si/Al = 15 | 10 Si/Al = 30 | 11 Si/Al = 40 | 12 Si/Al= 70 | 13 Si/Al = 100 |
|---|---|---|---|---|---|---|
| SiO$_2$ (mol) | 60 | 60 | 60 | 60 | 60 | 60 |
| Al$_2$O$_3$ (mol) | 2 | 2 | 1 | 0.75 | 0.43 | 0.3 |
| Na$_2$O (mol) | 10 | 10 | 10 | 10 | 5 | 5 |
| TMHMDA (mol) | 20 | 20 | 20 | 20 | 20 | 20 |
| CH$_3$I (mol) | 40 | 40 | 40 | 40 | 40 | 40 |
| H$_2$O (mol) | 2800 | 2800 | 2800 | 2800 | 2800 | 2800 |
| EU-1/SiO$_2$ (g/g) | 0 | 0.04 | 0.04 | 0.04 | 0.04 | 0.04 |

TMHMDA = 1-6 tetramethylhexamethylenediamine = Me$_2$N(CH$_2$)$_6$NMe$_2$

The preparation was the same as that described for Examples 1 to 7, with the addition of mixing the two starting precursors, 1–6 tetramethylhexamethylenediamine (Acros, 99%) and methyl iodide (Acros, 99%) in 80% of the water necessary for gel formation. The quantities of reactants introduced are shown in the following table:

| Example | 8 Si/Al = 15 | 9 Si/Al = 15 | 10 Si/Al = 30 | 11 Si/Al = 40 | 12 Si/Al = 70 | 13 Si/Al = 100 |
|---|---|---|---|---|---|---|
| Colloidal silica (g) | 14.07 | 14.07 | 14.10 | 14.10 | 14.18 | 14.18 |
| Sodium aluminate (g) | 0.69 | 0.694 | 0.347 | 0.261 | 0.150 | 0.105 |
| Sodium hydroxide (g) | 0.956 | 0.956 | 1.105 | 1.143 | 0.566 | 0.586 |
| TMHMDA (g) | 5.43 | 5.43 | 5.44 | 5.44 | 5.45 | 5.47 |
| CH$_3$I (g) | 8.97 | 8.97 | 8.99 | 8.99 | 9.04 | 9.04 |
| Water (g) | 69.87 | 69.87 | 70.02 | 70.06 | 70.59 | 70.61 |
| EU-1 seeds (g) | 0 | 0.225 | 0.226 | 0.226 | 0.227 | 0.227 |

TMHMDA = 1-6 tetramethylhexamethylenediamine = Me$_2$N(CH$_2$)$_6$NMe$_2$

The results of X ray diffraction and chemical analysis are shown in Table 2. The syntheses of Examples 9, 10, 11, 12 and 13 carried out at 180° C. with the prior art structuring agent with EU-1 seeds led to pure EU-1 zeolite (100%±3 crystallinity) with a Si/Al ratio which was between 15 and 100, in a maximum yield (about 5%). Example 8 corresponds to a preparation without seed and required a longer crystallisation period compared with Example 9 to produce the EU-1 zeolite (122 hours as opposed to 93 hours).

EXAMPLES 14 TO 20 (in accordance with the invention)

Synthesis of EU-1 zeolite (or TPZ-3) with a Si/Al ratio of 15 to 100 with specific precursors of hexamethonium iodide (1,6-hexamethylhexamethylenediammonium iodide) as the organic structuring agent containing a monoamine (trimethylamine and dibromohexane). The synthesis mixture had the following molar composition:

| Example | 14 Si/Al = 15 | 15 Si/Al = 15 | 16 & 17 Si/Al = 30 | 18 Si/Al = 40 | 19 Si/Al = 60 | 20 Si/Al = 100 |
|---|---|---|---|---|---|---|
| SiO$_2$ (mol) | 60 | 60 | 60 | 60 | 60 | 60 |
| Al$_2$O$_3$ (mol) | 2 | 2 | 1 | 0.75 | 0.43 | 0.3 |
| Na$_2$O (mol) | 10 | 10 | 10 | 10 | 5 | 5 |
| DBH (mol) | 20 | 20 | 20 | 20 | 20 | 20 |
| TMA (mol) | 40 | 40 | 40 | 40 | 40 | 40 |
| H$_2$O (mol) | 2800 | 2800 | 2800 | 2800 | 2800 | 2800 |
| EU-1/SiO$_2$ (g/g) | 0 | 0.04 | 0.04 | 0.04 | 0.04 | 0.04 |

DBH = dibromohexane
TMA = trimethylamine

The preparation was the same as that described for Examples 1 to 7, with the addition of mixing the two starting precursors, the aqueous solution of trimethylamine (Acros, 45%) and dibromohexane (Acros, 99%) in 80% of the water necessary for gel formation. The quantities of reactants introduced are shown in the following table:

| Example | 14 Si/Al = 15 | 15 Si/Al = 15 | 16 & 17 Si/Al = 30 | 18 Si/Al = 40 | 19 Si/Al = 60 | 20 Si/Al = 100 |
|---|---|---|---|---|---|---|
| Colloidal silica (g) | 14.50 | 14.50 | 14.52 | 14.53 | 14.61 | 14.61 |
| Sodium aluminate (g) | 0.715 | 0.715 | 0.358 | 0.269 | 0.180 | 0.108 |

-continued

| Example | 14 Si/Al = 15 | 15 Si/Al = 15 | 16 & 17 Si/Al = 30 | 18 Si/Al = 40 | 19 Si/Al = 60 | 20 Si/Al = 100 |
|---|---|---|---|---|---|---|
| Sodium hydroxide (g) | 0.985 | 0.985 | 1.139 | 1.177 | 0.573 | 0.604 |
| DBH (g) | 8.02 | 8.02 | 8.03 | 8.04 | 8.08 | 8.09 |
| TMA (g) | 8.45 | 8.45 | 8.46 | 8.47 | 8.51 | 8.52 |
| Water (g) | 67.3 | 67.33 | 67.48 | 67.52 | 68.04 | 68.07 |
| EU-1 seeds (g) | 0 | 0.232 | 0.232 | 0.232 | 0.234 | 0.234 |

DBH = dibromohexane
TMA = trimethylamine

The results of X ray diffraction and chemical analysis are shown in Table 3. The syntheses of Examples 15, 16, 18, 19 and 20 carried out at 180° C. with the specific structuring agents of the invention with EU-1 seeds led to pure EU-1 zeolite (100%±3 crystallinity) with a Si/Al ratio which was between 15 and 100, in a maximum yield (about 5%). Example 14 corresponds to a preparation without seed and required a longer crystallisation period compared with Example 15 to produce the EU-1 zeolite (110 hours as opposed to 85 hours). Example 17 produced mostly EU-1 with a little cristobalite because of a longer crystallisation period compared with Example 16 (82 hours as opposed to 65 hours).

TABLE 1

Syntheses of EU-1 zeolites with the prior art structuring agent

| Example n° | 1 | 2 | 3 | 4 | 5 | 6 | 7 |
|---|---|---|---|---|---|---|---|
| Gel | | | | | | | |
| Formulation | 60 $SiO_2$-a $Al_2O_3$-b $Na_2O$-20 $HxBr_2$-2800 $H_2O$-0–4% EU-1 | | | | | | |
| Si/Al = 30/a (mol/mol) | 15 | 15 | 30 | 30 | 40 | 70 | 100 |
| Alkalinity b (mol) | 10 | 10 | 10 | 10 | 10 | 5 | 5 |
| Seeds | No | Yes | Yes | Yes | Yes | Yes | Yes |
| Crystallisation | | | | | | | |
| Temperature (° C.) | 180 | | | | | | |
| Time (h) | 125 | 96 | 72 | 96 | 72 | 72 | 60 |
| Solid | | | | | | | |
| Phase (XRD) | 100% EU-1 | 101% EU-1 | 100% EU-1 | 90% EU-1 + 10% | 98% EU-1 | 99% EU-1 | 102% EU-1 |
| | | | | CRISTO | | | |
| Si/Al (XF) | 14.2 | 13.9 | 26.6 | nd | 36.9 | 68.6 | 90.7 |
| Solid yield (%) | 5.1 | 5.8 | 5.2 | 5.3 | 5.1 | 5.6 | 5.2 |

CRISTO: cristobalite
$HxBr_2$ = hexamethonium bromide = $Me_3N(CH_2)_6N\ Me_3^{2+}(Br^-)_2$
XRD: X ray diffraction with Example 1 as reference
XF: X ray fluorescence

TABLE 2

Syntheses of EU-1 zeolites with the prior organic structuring agents

| Example n° | 8 | 9 | 10 | 11 | 12 | 13 |
|---|---|---|---|---|---|---|
| Gel | | | | | | |
| Formulation | 60 $SiO_2$-a $Al_2O_3$-b $Na_2O$-20 TMHDA-40 $CH_3I$-2800 $H_2O$-4% EU-1 | | | | | |
| Si/Al = 30/a (mol/mol) | 15 | 15 | 30 | 40 | 70 | 1000 |
| Alkalinity b (mol) | 10 | 10 | 10 | 10 | 5 | 5 |
| Crystallisation | | | | | | |
| Temperature (° C.) | 180 | | | | | |
| Time (h) | 122 | 93 | 70 | 70 | 70 | 60 |
| Solid | | | | | | |
| Phase (XRD) | 100% EU-1 | 99% EU-1 | 98% EU-1 CRISTO | 101% EU-1 | 100% EU-1 | 98% EU-1 |
| Si/Al (XF) | 14.2 | 13.8 | 13.2 | 13.7 | 14.3 | 13.5 |
| Solid yield (%) | 5.0 | 5.2 | 4.8 | 5.6 | 5.4 | 5.1 |

TMHMDA = 1-6 tetramethylhexamethylenediamine = $Me_2N(CH_2)_6NMe_2$
XRD: X ray diffraction with Example 1 as reference
XF: X ray fluorescence

TABLE 3

Syntheses of EU-1 zeolites with organic structuring agent precursors in accordance with the invention

| Example n° | 14 | 15 | 16 | 17 | 18 | 19 | 20 |
|---|---|---|---|---|---|---|---|
| Gel | | | | | | | |
| Formulation | 60 $SiO_2$-a $Al_2O_3$-b $Na_2O$-20 DBrH-40 TMA-2800 $H_2O$-0–4% EU-1 | | | | | | |
| Si/Al = 30/a (mol/mol) | 15 | 15 | 30 | 30 | 40 | 60 | 100 |
| Alkalinity b (mol) | 10 | 10 | 10 | 10 | 10 | 5 | 5 |
| Seeds | No | Yes | Yes | Yes | Yes | Yes | Yes |
| Crystallisation | | | | | | | |
| Temperature (° C.) | 180 | | | | | | |
| Time (h) | 110 | 85 | 65 | 82 | 65 | 65 | 53 |

TABLE 3-continued

Syntheses of EU-1 zeolites with organic structuring agent precursors in accordance with the invention

| Example n° | 14 | 15 | 16 | 17 | 18 | 19 | 20 |
|---|---|---|---|---|---|---|---|
| Solid | | | | | | | |
| Phase (XRD) | 100% EU-1 | 102% EU-1 | 101% EU-1 | 90% EU-1 + 10% CRISTO | 99% EU-1 | 100% EU-1 | 98% EU-1 |
| Si/Al (XF) | 14.4 | 14.2 | 25.4 | nd | 34.6 | 57.6 | 92.3 |
| Solid yield (%) | 5.5 | 5.0 | 5.5 | 5.2 | 5.6 | 5.7 | 5.8 |

CRISTO: cristobalite
DBH = dibromohexane
TMA = trimethylamine
XRD: X ray diffraction with Example 14 as reference
XF: X ray fluorescence Summary of EU-1 syntheses The data given in Tables 1, 2 and 3 show that the EU-1 zeolites synthesised using specific organic structuring agent precursors containing a monoamine were crystallised in a shorter time than the EU-1 zeolites synthesised by a prior art method, which produced a cost advantage. Further, adding zeolite seeds during preparation further improved the performance as regards crystallisation time.

EXAMPLE 21

Preparation of a Catalyst A, not in Accordance with the Invention, Containing the EU-1 Zeolite of Example 1 and 0.3% by Weight of Platinum The starting material used was as synthesised EU-1 zeolite as described in Example 1, comprising the organic structuring agent, silicon and aluminium, with an overall Si/Al atomic ratio of 14.2 and a sodium content of about 1.5% with respect to the weight of EU-1 zeolite.

This EU-1 zeolite first underwent dry calcining at 550° C. in a stream of air for 6 hours. The solid obtained underwent three ion exchange steps in a 10 N $NH_4NO_3$ solution at about 100° C. for 4 hours for each exchange.

At the end of these treatments, the EU-1 zeolite in its $NH_4$ form had an overall Si/Al atomic ratio of 18.8 and a sodium content of 50 ppm by weight with respect to the weight of dry EU-1 zeolite.

The EU-1 zeolite was then formed by extrusion with an alumina gel to obtain, after drying and calcining in dry air, a support S1 constituted by 1.4 mm diameter extrudates containing 10% by weight of EU-1 zeolite in the H form and 90% of alumina.

The support S1 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst A produced contained, by weight, 10.0% of EU-1 zeolite in its hydrogen form, 89.7% of alumina and 0.3% of platinum.

EXAMPLE 22

Preparation of a Catalyst B, not in Accordance with the Invention, Containing the EU-1 Zeolite of Example 2 and 0.3% by Weight of Platinum The starting material used was as synthesised EU-1 zeolite as described in Example 2, comprising the organic structuring agent, silicon and aluminium, with an overall Si/Al atomic ratio of 13.9 and a sodium content of about 1.5% with respect to the weight of EU-1 zeolite.

This EU-1 zeolite first underwent dry calcining at 550° C. in a stream of air for 6 hours. The solid obtained underwent three ion exchange steps in a 10 N $NH_4NO_3$ solution at about 100° C. for 4 hours for each exchange.

At the end of these treatments, the EU-1 zeolite in its $NH_4$ form had an overall Si/Al atomic ratio of 18.5 and a sodium content of 45 ppm by weight with respect to the weight of dry EU-1 zeolite.

The EU-1 zeolite was then formed by extrusion with an alumina gel to obtain, after drying and calcining in dry air, a support S2 constituted by 1.4 mm diameter extrudates containing 10% by weight of EU-1 zeolite in the H form and 90% of alumina.

The support S2 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst B produced contained, by weight, 10.0% of EU-1 zeolite in its hydrogen form, 89.7% of alumina and 0.3% of platinum.

EXAMPLE 23

Preparation of Catalyst C, in Accordance with the Invention, Containing the EU-1 Zeolite of Example 14 and 0.3% by Weight of Platinum The starting material used was as synthesised EU-1 zeolite as described in Example 14, comprising the organic structuring agent, silicon and aluminium, with an overall Si/Al atomic ratio of 14.4 and a sodium content of about 1.5% with respect to the weight of EU-1 zeolite.

This EU-1 zeolite first underwent dry calcining at 550° C. in a stream of air for 6 hours. The solid obtained underwent three ion exchange steps in a 10 N $NH_4NO_3$ solution at about 100° C. for 4 hours for each exchange.

At the end of these treatments, the EU-1 zeolite in its $NH_4$ form had an overall Si/Al atomic ratio of 18.7 and a sodium content of 30 ppm by weight with respect to the weight of dry EU-1 zeolite.

The EU-1 zeolite was then formed by extrusion with an alumina gel to obtain, after drying and calcining in dry air, a support S3 constituted by 1.4 mm diameter extrudates containing 10% by weight of EU-1 zeolite in the H form and 90% of alumina.

The support S3 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst C produced contained, by weight, 10.0% of EU-1 zeolite in its hydrogen form, 89.7% of alumina and 0.3% of platinum.

EXAMPLE 24

Preparation of a Catalyst D, in Accordance with the Invention, Containing the EU-1 Zeolite of Example 15 and 0.3% by Weight of Platinum The starting material used was as synthesised EU-1 zeolite as described in Example 15, comprising the organic structuring agent, silicon and aluminium, with an overall Si/Al atomic ratio of 14.2 and a sodium content of about 1.5% with respect to the weight of EU-1 zeolite.

This EU-1 zeolite first underwent dry calcining at 550° C. in a stream of air for 6 hours. The solid obtained underwent three ion exchange steps in a 10 N $NH_4NO_3$ solution at about 100° C. for 4 hours for each exchange.

At the end of these treatments, the EU-1 zeolite in its $NH_4$ form had an overall Si/Al atomic ratio of 18.6 and a sodium content of 40 ppm by weight with respect to the weight of dry EU-1 zeolite.

The EU-1 zeolite was then formed by extrusion with an alumina gel to obtain. after drying and calcining in dry air, a support S4 constituted by 1.4 mm diameter extrudates containing 10% by weight of EU-1 zeolite in the H form and 90% of alumina.

The support S4 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst D produced contained, by weight, 10.0% of EU-1 zeolite in its hydrogen form, 89.7% of alumina and 0.3% of platinum.

EXAMPLE 25

Preparation of a Catalyst E, not in Accordance with the Invention, Containing the EU-1 Zeolite of Example 8 and 0.3% by Weight of Platinum The starting material used was as synthesised EU-1 zeolite as described in Example 8, comprising the organic structuring agent, silicon and aluminium, with an overall Si/Al atomic ratio of 14.2 and a sodium content of about 1.5% with respect to the weight of EU-1 zeolite.

This EU-1 zeolite first underwent dry calcining at 550° C. in a stream of air for 6 hours. The solid obtained underwent three ion exchange steps in a 10 N $NH_4NO_3$ solution at about 100° C. for 4 hours for each exchange.

At the end of these treatments, the EU-1 zeolite in its $NH_4$ form had an overall Si/Al atomic ratio of 18.7 and a sodium content of 40 ppm by weight with respect to the weight of dry EU-1 zeolite.

The EU-1 zeolite was then formed by extrusion with an alumina gel to obtain, after drying and calcining in dry air, a support S5 constituted by 1.4 mm diameter extrudates containing 10% by weight of EU-1 zeolite in the H form and 90% of alumina.

The support S5 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst E produced contained, by weight, 10.0% of EU-1 zeolite in its hydrogen form, 89.7% of alumina and 0.3% of platinum.

EXAMPLE 26

Preparation of a Catalyst F, not in Accordance with the Invention, Containing the EU-1 Zeolite of Example 9 and 0.3% by Weight of Platinum The starting material used was as synthesised EU-1 zeolite as described in Example 9, comprising the organic structuring agent, silicon and aluminium, with an overall Si/Al atomic ratio of 13.8 and a sodium content of about 1.5% with respect to the weight of EU-1 zeolite.

This EU-1 zeolite first underwent dry calcining at 550° C. in a stream of air for 6 hours. The solid obtained underwent three ion exchange steps in a 10 N $NH_4NO_3$ solution at about 100° C. for 4 hours for each exchange.

At the end of these treatments, the EU-1 zeolite in its N form had an overall Si/Al atomic ratio of 18.4 and a sodium content of 45 ppm by weight with respect to the weight of dry EU-1 zeolite.

The EU-1 zeolite was then formed by extrusion with an alumina gel to obtain, after drying and calcining in dry air, a support S6 constituted by 1.4 mm diameter extrudates containing 10% by weight of EU-1 zeolite in the H form and 90% of alumina.

The support S6 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst F produced contained, by weight, 10.0% of EU-1 zeolite in its hydrogen form, 89.7% of alumina and 0.3% of platinum.

EXAMPLE 27

Evaluation of Catalytic Properties of Catalysts A, B, C, D, E and F by Isomerising an Aromatic C8 Cut The performances of catalysts A, B, C, D, E and F were evaluated by isomerising an aromatic C8 cut principally containing meta-xylene, ortho-xylene and ethylbenzene. The operating conditions were as follows:

temperature: 390° C.

total pressure: 15 bar, (1 bar=0.1 MPa);

hydrogen partial pressure: 12 bar.

The catalysts were first treated with a feed containing dimethyl disulphide (DMDS) in the presence of hydrogen, with a concentration such that the sulphur/metal atomic ratio was 1.5. The catalyst was then maintained for 3 hours at 400° C. in a stream of hydrogen then the feed was injected.

The catalysts were laboratory tested, using 5 g and with no hydrogen recycle.

The catalysts were compared in terms of their activity (by approximate equilibria of paraxylene and ethylbenzene, and by ethylbenzene conversion) and their selectivity by net losses at iso-approximate equilibrium of para-xylene.

Side reactions lead to three types of losses: losses to paraffins essentially resulting from naphthene ring opening reactions followed by cracking; losses to aromatics formed by dismutation and transalkylation of aromatic compounds containing 8 carbon atoms (AC8) and finally, losses to naphthalenes, namely naphthenes containing 8 carbon atoms (N8) due to hydrogenation of aromatic compounds. N8 can be recycled, so the losses by cracking and dismutation/transalkylation including naphthenes other than N8 are compared (the sum of which constitutes net losses) taking a base of 100 for the net losses of catalyst A, not in accordance with the invention.

In order to calculate the approximate equilibrium (AEQ), the concentrations of para-xylenes (% pX) are expressed with respect to the three xylene isomers.

The approximate equilibrium (AEQ) is defined as follows:

$$pXAEQ\ (\%) = 100 \times (\%\ PX_{effluent} - \%\ PX_{feed}) / (\%\ PX_{equilibrium} - \%\ PX_{feed})$$

The cracking losses (P1) are the AC8 losses in the form of C1 to C8 paraffins (PAR):

$$P1\ (wt\ \%) = 100 \times [(\%\ PAR_{effluent} \times \text{weight of effluent}) - (\%\ PAR_{feed} \times \text{weight of feed})] / (\%\ AC8_{feed} \times \text{weight of feed})$$

The dismutation/transalkylation losses (P2) are the AC8 losses in the form of naphthenes other than N8, toluene, benzene and C9+aromatics (OAN):

$$P2\ (wt\ \%) = 100 \times [(\%\ OAN_{effluent} \times \text{weight of effluent}) - (\%\ OAN_{feed} \times \text{weight of feed})] / (\%\ AC8_{feed} \times \text{weight of feed})$$

The sum of losses P1 and P2 represents the net losses.
The data shown in Table 4 were obtained under iso-experimental conditions.

TABLE 4

| Catalysts | A (comp) | B (comp) | C (inv) | D (inv) | E (comp) | F (comp) |
|---|---|---|---|---|---|---|
| pX AEQ (%) | 98.1 | 98.3 | 98.0 | 97.8 | 98.3 | 98.2 |
| EB conversion (%) | 59.6 | 58.8 | 59.5 | 59.3 | 59.4 | 59.6 |

It can be seen from the results shown in Table 4 that catalysts C and D of the invention lead to results which are comparable with those obtained with catalysts A, B, E and F which are not in accordance with the invention.

Further, these catalysts were compared at a lower pX AEQ (about 95.5%) by varying the mass flow rate of the feed. These results are shown in Table 5.

TABLE 5

| Catalysts | A | B | C | D | E | F |
|---|---|---|---|---|---|---|
| pX AEQ (%) | 95.5 | 95.2 | 95.7 | 95.1 | 95.5 | 95.3 |
| Net losses (wt %) | 4.9 | 4.7 | 5.0 | 4.6 | 4.8 | 4.9 |

At a lower iso pX AEQ, Table 5 confirms the previous results in Table 4 and shows that the catalysts are all selective as well.

The activity and selectivity obtained during use of catalysts C and D, based on zeolites with structure type EUO, obtained using precursors of the organic structuring agent for isomerisation of an aromatic C8 cut are thus comparable with those of catalysts containing zeolites with structure type EUO with a similar Si/Al ratio and obtained using a synthesis mode during which the organic structuring agent itself is used as described in the prior art. This result is also verified in the case of the use of precursors containing a diamine.

Finally, catalysts A, B, C, D, E and F were compared as regards stability over time under the experimental conditions described at the beginning of the example and over a duration of 400 hours.

Stability was evaluated from the evolution of ethylbenzene conversion. The results are shown in Table 6.

TABLE 6

| Catalysts | A | B | C | D | E | F |
|---|---|---|---|---|---|---|
| EB conversion (%) at t = 36 h | 59.6 | 59.8 | 59.5 | 59.3 | 59.4 | 59.6 |
| EB conversion (%) at t = 400 h | 57.6 | 57.7 | 57.3 | 57.4 | 57.5 | 57.6 |
| Drop in EB conversion (%) | 3.3 | 3.5 | 3.6 | 3.2 | 3.2 | 3.4 |

It can be seen that the deactivation of the six catalysts A, B, C, D, E and F over 400 hours was comparable.

The catalytic properties (activity, selectivity and stability) of the six catalysts are comparable. Introducing this novel mode of synthesising zeolite with structure type EUO in the preparation of this catalyst for isomerising aromatic C8 cuts is thus a substantial advantage as regards cost since the precursors are cheaper and the zeolite synthesis time is reduced while the catalytic properties are preserved. Further, the use of these precursors of the structuring agent containing a monoamine limits toxicity risks.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French applications 98/13.773 and 98/16.411, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for synthesizing a zeolitic material with structure type EUO comprising at least one element X selected from silicon and germanium and at least one element T selected from aluminum, iron, gallium, boron, titanium, vanadium, zirconium, molybdenum, arsenic, antimony, chromium, and manganese, comprising reacting an aqueous mixture of at least one source of at least one element X, at least one source of at least one element T and at least one monoamine, wherein said monoamine is a precursor of a structuring agent comprising an alkylated polymethylene α-ω diammonium derivative.

2. A process according to claim 1, in which the alkylated polymethylene α-ω diammonium derivative has the following formula: $R_1R_2R_3N^+(CH_2)_nN^+R_4R_5R_6$, where n is in the range 3 to 14 and $R_1$ to $R_6$, which may be identical or different, can represent alkyl or hydroxyalkyl radicals containing 1 to 8 carbon atoms; up to five $R_1$ to $R_6$ radicals possibly being hydrogen.

3. A process according to claim 1, in which the alkylated polymethylene α-ω diammonium derivative is an alkylated hexamethylenediammonium compound.

4. A process according to claim 1, in which the alkylated polymethylene α-ω diammonium derivative is a 1,6-N,N,N,N',N',N'-hexamethylhexamethylenediammonium salt.

5. A process according to claim 1, in which the monoamine is a trialkylamine.

6. A process according to claim 1, in which the monoamine is trimethylamine (TMA).

7. A process according to claim 1, wherein the aqueous mixture further comprises at least one further alkylated polymethylene α-ω diammonium derivative of at least one dihalide agent or at least one alkanediol.

8. A process according to claim 7, in which the precursor is dibromohexane.

9. A process according to claim 7, in which the precursor of the alkylated polymethylene α-ω diammonium derivative is introduced at any point in the synthesis.

10. A process according to claim 7, in which the precursor is introduced in solution before adding the element T and element X.

11. A process according to claim 7, in which the reaction mixture has the following molar composition, expressed in the oxide form:

| | |
|---|---|
| $XO_2/T_2O_3$ (mol/mol) | at least 10 |
| $Q/WO_2$ (mol/mol) | 0.002 to 2.0 |
| $OH^-/XO_2$ (mol/mol) | 0.002 to 2.0 |
| $Q/(M^+ + Q)$ (mol/mol) | 0.1 to 1 |
| $H_2O/XO_2$ (mol/mol) | 1 to 500 |
| $P/XO_2$ (mol/mol) | 0 to 5 |
| $S/XO_2$ (g/g) | 0 to 0.1 | where $M^+$ represents an alkali metal or ammonium and Q represents the alkylated polymethylene α-ω diammonium derivative, introduced by means of a first precursor comprising a monoamine and a second precursor comprising an alkane dihalide or an alkanediol.

12. A process according to claim 1, in which at least one seed of at least one zeolite is added to the reaction mixture.

13. A process according to claim 1, in which at least one salt P is added to the mixture.

14. A process according to claim 1, in which the reaction mixture has the following molar composition, expressed in the oxide form:

| | |
|---|---|
| $XO_2/T_2O_3$ (mol/mol) | at least 10 |
| $Q/XO_2$ (mol/mol) | 0.002 to 2.0 |
| $OH^-/XO_2$ (mol/mol) | 0.002 to 2.0 |
| $Q/(M^+ + Q)$ (mol/mol) | 0.1 to 1 |
| $H_2O/XO_2$ (mol/mol) | 1 to 500 |
| $P/XO_2$ (mol/mol) | 0 to 5 |
| $S/XO_2$ (g/g) | 0 to 0.1 | where $M^+$ represents an alkali metal or ammonium and Q represents the alkylated polymethylene α-ω diammonium derivative, partly introduced by means of at least one precursor comprising said monoamine.

15. A process according to claims 1, in which X is silicon and T is aluminium.

16. A process according to claim 1, in which the precursor of the alkylated polymethylene α-ω diammonium derivative is introduced at any point in the synthesis.

17. A process according to claim 1, in which the precursor is introduced in solution before adding the element T and element X.

18. In a process comprising separating a gaseous component in contact with a zeolite, the improvement wherein said zeolite is a zeolite with structure type EUO produced according to claim 1.

* * * * *